United States Patent [19]

Iida et al.

[11] 4,259,859
[45] Apr. 7, 1981

[54] METHOD FOR DETERMINATION OF THERMAL PROPERTIES BY ARBITRARY HEATING

[75] Inventors: Yoshihiro Iida, 1722-4 Koshigoe, Kamakura-shi Kanagawa-ken, Japan; Haruhiko Shigeta; Hisao Akimoto, both of Yokohama, Japan

[73] Assignees: Yoshihiro Iida, Kamakura; Showa Denko K.K., Tokyo, both of Japan

[21] Appl. No.: 35,717

[22] Filed: May 3, 1979

[51] Int. Cl.³ .............................................. G01N 25/18
[52] U.S. Cl. .................................................. 73/15 A
[58] Field of Search .................... 73/15 A, 340, 15 FD

[56] References Cited

PUBLICATIONS

Beck et al.; Int. J. Heat Mass Transfer, 20 (1977), pp. 259-267.
Tye, Thermal Conductivity, vol. 1-2, (1969), Academic Press.
Kobayashi, JSME, 77-668 (1974), p. 754.

*Primary Examiner*—Donald O. Woodiel
*Attorney, Agent, or Firm*—Oblon, Fisher, Spivak, McClelland & Maier

[57] ABSTRACT

A method for the determination of thermal properties by arbitrary heating, comprising the steps of measuring temperature responses at several points on a given sample, calculating Laplace integrals of the temperature responses and subjecting the integrals to the Laplace transformed heat conduction equation and thereby determining the thermal properties such as thermal conductivity, thermal diffusivity and thermal capacity.

14 Claims, 20 Drawing Figures

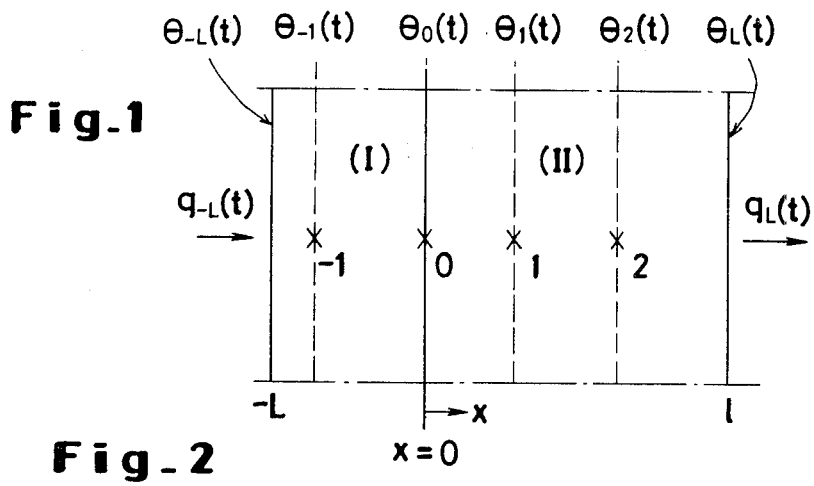
Fig. 1
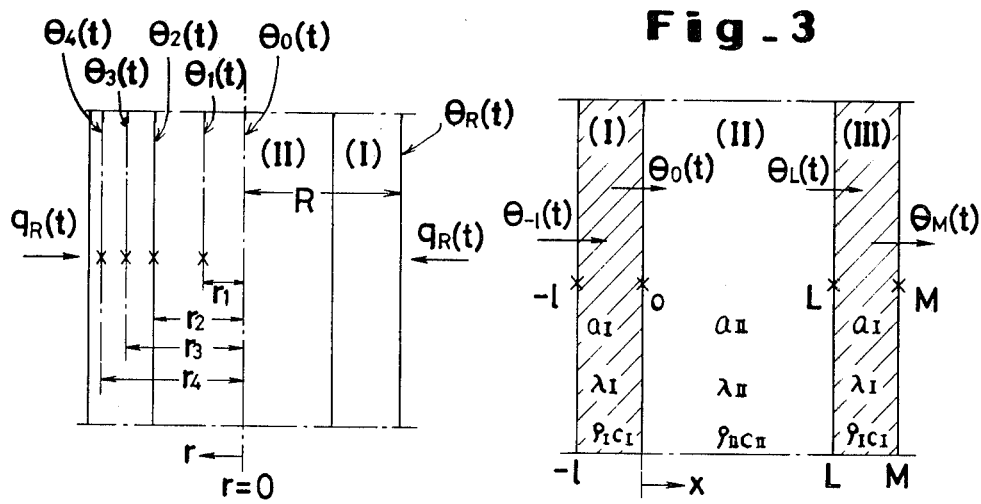
Fig. 2
Fig. 3
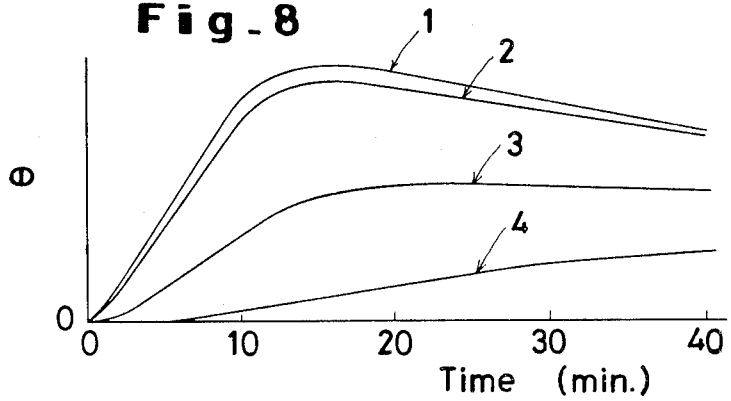
Fig. 8

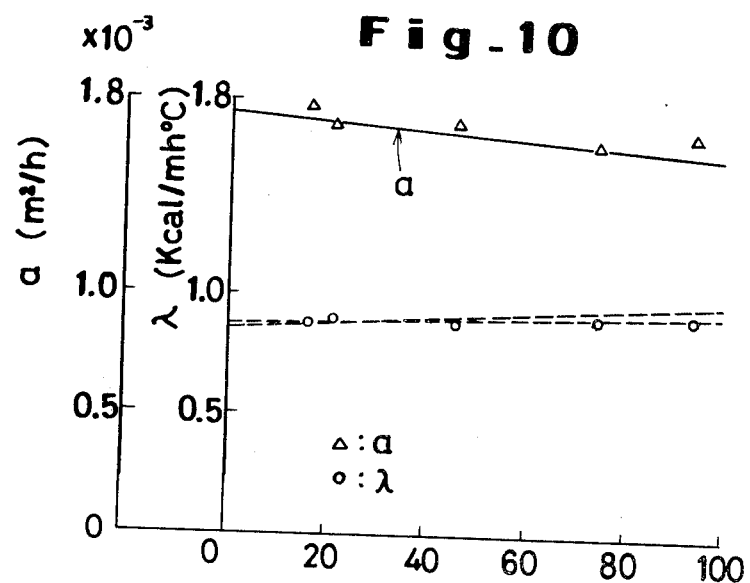
Fig_10
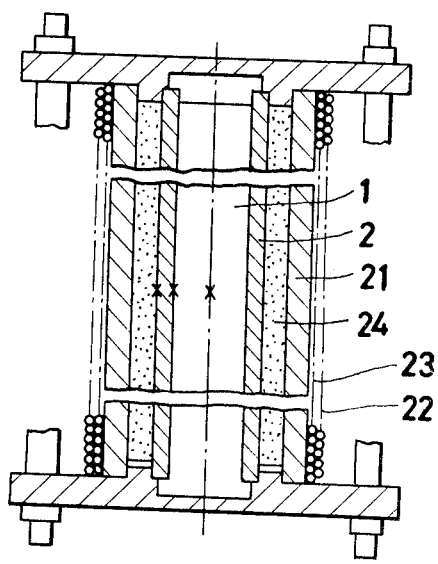
Fig_11
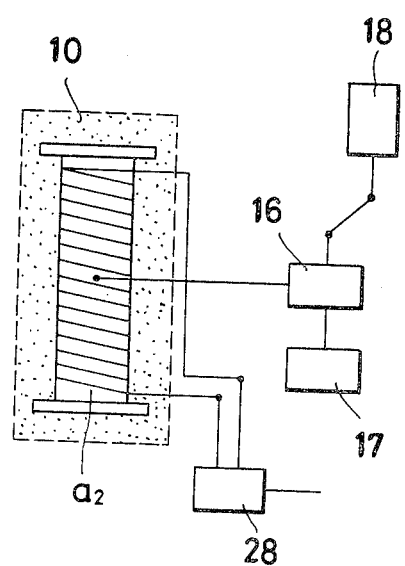
Fig_12

○ : Sylindlical Sample
□ : Plate-Shaped Sample
▓ : Data in Reported Test

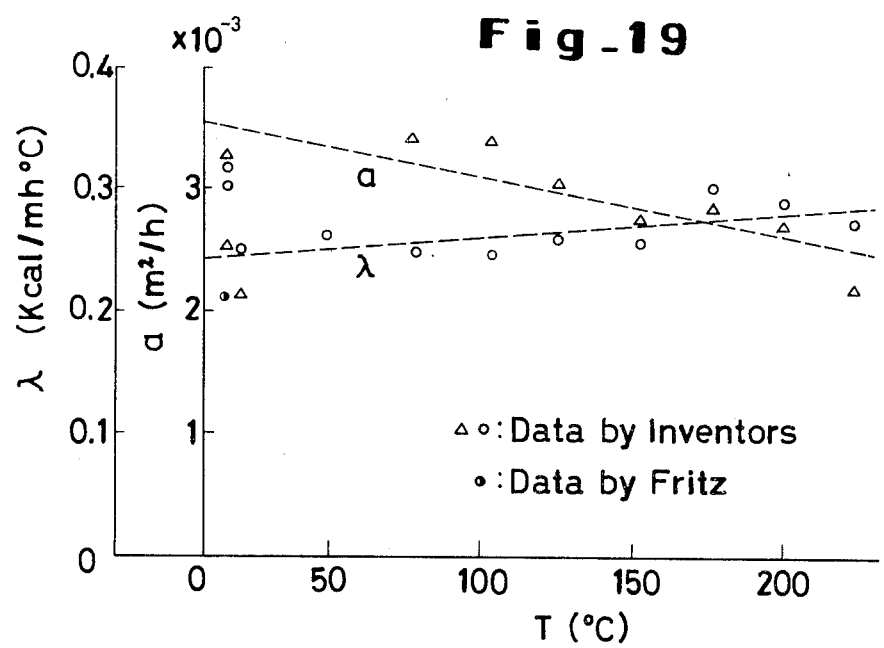
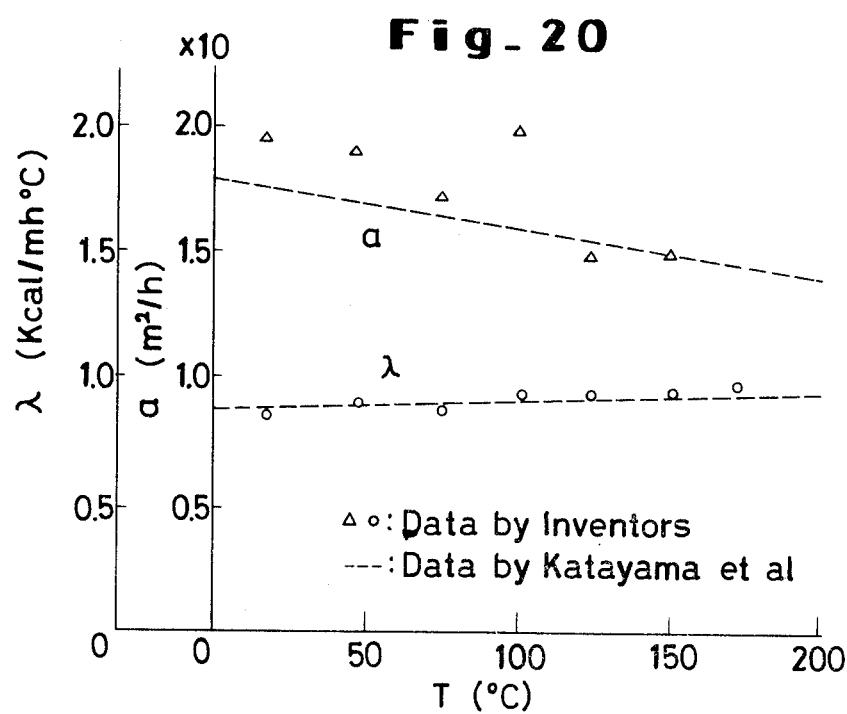

METHOD FOR DETERMINATION OF THERMAL PROPERTIES BY ARBITRARY HEATING

BACKGROUND OF THE INVENTION:

This invention relates to a method for the determination of thermal properties such as thermal conductivity, thermal diffusivity and thermal capacity by arbitrary heat input under an arbitrary boundary condition and under arbitrary initial conditions, with the initial temperature distribution kept in a certain limited condition.

For virtually all industries, especially those currently being urged to adopt effective measures concerning the consumption of energy, and for various academic branches in the natural sciences as well, the numerical values of thermal properties have great significance. The methods heretofore practiced in the determination of thermal properties are broadly divided into a steady method and a non steady method which is based on the analytical solution of the basic heat conduction equation. The steady method (reviewed by Tye, R. P., Thermal Conductivity, Vol. 1-2 (1969), Academic Press) has found widespread acceptance. Nevertheless, this method entails a practical difficulty in having the temperature maintained in a necessary steady state. The measurement by this method takes much time and calls for advanced skill.

The non steady method which is based on analytical solution (reviewed Kobayashi, K., J. of JSME, 77-668 (1974), 754) has recently achieved a notable growth in acceptance. To materialize experimentally the ideal boundary condition used for obtaining the analytical solution, meticulous care is needed and the apparatus used therefor is generally complicated and expensive. The characteristic common to the various methods described above resides in the difficulty experienced in establishing the boundary condition of the given sample with an ideal steady condition, stepped value and so on. This fact has made the determination of thermal properties extremely difficult.

To meet today's need for accurate data on thermal properties, there must be provided a method which is capable of reducing the necessity for establishing the boundary condition. As one such method, there may be cited the method which is based on the numerical calculation. With this method, however, the arbitrariness is limited and the calculation is fairly complicated. At this stage, there is no indication that this method will find popular acceptance.

The only proposed method (Kavianipour, A. and Beck, J. V., Int. J. Heat Mass Transfer, 20, (1977), 259) which involves a principle similar to the principle of the present invention is intended for sole application to semi-infinite solid articles as the subject of determination. For the purpose of simultaneous determination, this method inevitably involves bringing the given sample into abrupt contact with an article of an elevated temperature and calculating the change in the heat flow rate on the basis of the average temperature change occurring in that article. Thus, the boundary condition involved therein can hardly be called perfectly arbitrary. Moreover, the range of determination allowable by this method is limited and the method itself suffers from the disadvantage that the determination admits of a heavy error due to heat loss and other factors.

The development of a method which, unlike the conventional method, permits thermal properties to be determined by a procedure comparable with any of the conventionally practiced procedures in a system wherein the boundary condition is perfectly arbitrary and the heating condition is also entirely arbitrary can be expected to make a notable improvement in terms of equipment, process and accuracy.

SUMMARY OF THE INVENTION

An object of the present invention is to provide a method for the determination of thermal properties in a system involving basically and perfectly arbitrary boundary and heating conditions, whereby the range of conditions allowable for the determination is broadened, the apparatus used thereof enjoys simplicity of structure, the procedure involved is free from difficulty and the accuracy of determination is high.

Another object of the present invention is to provide a practical method for the determination of thermal properties which, unlike the conventional method, obviates such peripheral technical problems as the need for fabrication of samples and incorporation of thermometric elements while minimizing manual labor and yet enjoying high accuracy of determination.

BRIEF EXPLANATION OF THE DRAWING

FIG. 1 is an explanatory diagram illustrating the principle of the method of this invention for the determination of thermal properties of an infinite plate-shaped sample.

FIG. 2 is an explanatory diagram illustrating the principle of the method of this invention for the simultaneous determination of thermal properties of a cylindrical solid or hollow sample.

FIG. 3 is an explanatory diagram illustrating the principle of another preferred embodiment of this invention for the simultaneous determination of thermal properties.

FIG. 8 is a diagram illustrating time-course change of temperature (thermal electromotive force) at the points of measurement.

FIG. 10 is a diagram showing thermal properties of a soda glass plate.

FIG. 11 is a schematic diagram illustrating one typical test used for testing a cylindrical solid or hollow sample.

FIG. 12 is a schematic diagram illustrating one typical test apparatus using the test unit of FIG. 11.

FIG. 19 is a diagram showing the results of the determination of thermal properties of Teflon.

FIG. 20 is a diagram showing the results of the determination of thermal properties of soda glass.

DETAILED DESCRIPTION OF PREFERRED EMBODIMENT

Figure 4:
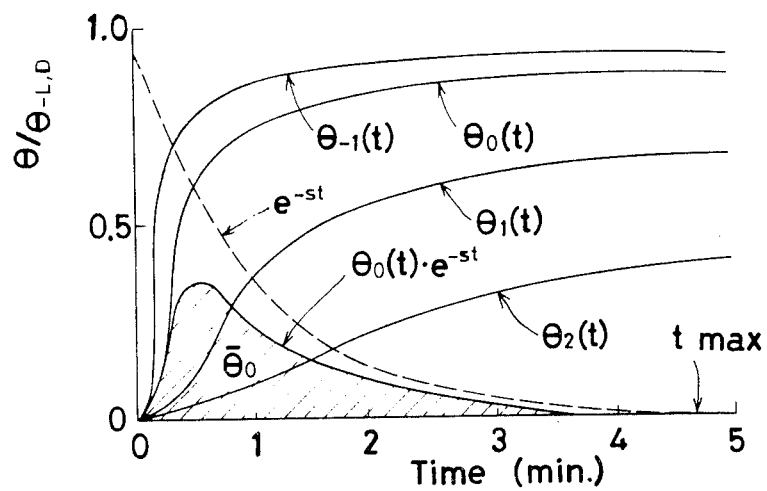
FIG. 4 is a diagram showing various thermal properties vs. change in temperature.

Now the present invention is described with reference to the basic principle of simultaneous determination of thermal properties by use of a plate-shaped sample illustrated in FIG. 1.

FIG. 1 illustrates a standard sample (I) (with thermal conductivity $\lambda_I$, thermal diffusivity $a_I$ and thermal capacity $\rho_I c_I$ known in advance) having a thickness of L and a given sample (II) (with $\lambda_{II}$, $a_{II}$ and $\rho_{II} c_{II}$ all unknown) having a thickness of l held in mutual contact with each other, so that the heat flow occurs in the direction perpendicular to the surface of contact. The results of determination are plotted as indicated in FIG. 1.

Let T and stand for temperature and t for time, and the thermal conductivity will be expressed by the following basic equation.

$$\frac{\partial T(x,t)}{\partial t} = a \frac{\partial^2 T(x,t)}{\partial x^2} \tag{1}$$

Now let T (x, o) stand for initial temperature distribution and take into consideration the factor "temperature difference" such as is expressed by the equation (2) given below, and the equation (1) will convert itself into the equation (3).

$$\theta(x,t) = T(x,t) - T(x,o) \tag{2}$$

$$\frac{\partial \theta(x,t)}{\partial t} = a \frac{\partial^2 \theta(x,t)}{\partial x^2} + a \frac{\partial^2 T(x,o)}{\partial x^2} \tag{3}$$

Assume that $T_o = T(o, o)$ is constant in the equation (3), and there will be derived the equation (4).

$$T(x,o) = mx = T_o \tag{4}$$

If the initial temperature distribution is uniform (m=o) or in a linear state, then the following equation is obtained.

$$\frac{\partial \theta(x,t)}{\partial t} = a \frac{\partial^2 \theta(x,t)}{\partial x^2} \tag{5}$$

By subjecting the equation (5) to Laplace transform, substituting $\theta$ (x, o)=0 in the resultant equation, and converting it to a normal differential equation, one obtains the following equation.

$$\frac{d^2 \overline{\theta}}{dx^2} - \frac{s}{a} \overline{\theta} = 0 \tag{6}$$

In this equation, s stands for Laplace parameter and $\overline{\theta}$ for the Laplace integral defined by the equation (7) below.

$$\overline{\theta} = \int_0^\infty e^{-st} \theta(x,t) \, dt \tag{7}$$

The general solution of the equation (6) is expressed by the equation (8).

$$\overline{\theta} = A_e \sqrt{s/a}\, x + B_e - \sqrt{s/a}\, x = AX + BX^{-1} \tag{8}$$

In this equation, X has the following meaning.

$$X = e \sqrt{s/a}\, x \tag{9}$$

In this connection, the Laplace integral $\overline{\theta}_i$ of the temperature response $\theta_i(t)$ at the position "i" ($i = -1, 0, 1, 2$) indicated in FIG. 1 is calculated in accordance with the equation (10).

$$\overline{\theta}_i = \int_0^\infty e^{-st} \theta_i(t)\, dt \tag{10}$$

On the other hand, the heat flux q (x, t) is expressed in accordance with Fourier's Equation as follows.

$$q(x,t) = -\lambda \frac{\partial \theta(x,t)}{\partial x} \tag{11}$$

By Laplace transform, the equation (11) is converted as shown below.

$$\overline{q} = -\lambda \frac{d\overline{\theta}}{dx} \tag{12}$$

Substitution of the equation (8) in the equation (12) results in the following equation.

$$\overline{q} = \lambda \sqrt{s/a} \, (-A_e \sqrt{s/a}\, x + B_e - \sqrt{s/a}\, x) \tag{13}$$

These are the basic relations that underlie the method of this invention.

It is proposed to consider these basic relations with respect to the standard sample (I). Since the integral constants $A_I$ and $B_I$ are fixed by calculating the values of $\overline{\theta}_i$ at the positions $i = -1, 0$ in accordance with the equation (10) and substituting the found values in the equation (8), the value of $(\overline{q}_o)_x$ at the position i=0 or in the surface of boundary, which is obtained by substituting the aforementioned integral constants in the equation (13), is expressed as follows.

$$(\overline{q}_o)_I = \lambda_I \sqrt{\frac{s}{a_I}} \left( \frac{\overline{\theta}_o(X_{-1} + 1/X_{-1}) - 2\overline{\theta}_{-1}}{X_{-1} - 1/X_{-1}} \right) \tag{14}$$

In this equation, $X_{-1}$ has the following meaning.

$$X_{-1} = e \sqrt{s/a}\, x_{-1}$$

Similarly, $(\overline{q}_o)_{II}$ for the positions i=0 and 1 (or 2) with respect to the given sample (II) is obtained as shown below.

$$(\bar{q}_o)_{II} = \lambda_{II} \sqrt{\frac{s}{a_{II}}} \left( \frac{\bar{\theta}_o(X_1 + 1/X_1) - 2\bar{\theta}_1}{X_1 - 1/X_1} \right) \quad (15)$$

In this equation, $X_1$ has the following meaning.

$$X_1 = e^{\sqrt{s/a_{II}}\, x_1}$$

Since obviously $(\bar{q}_o)_I = (\bar{q}_o)_{II}$, the following equation results from equalizing the equations (14) and (15) and making necessary rearrangements.

$$\frac{\lambda_{II}}{\lambda_I} = \sqrt{\frac{a_{II}}{a_I}} \left( \frac{X_1 - 1/X_1}{X_{-1} - 1X_{-1}} \right) \quad (16)$$

$$\left( \frac{\bar{\theta}_o(X_{-1} + 1/X_{-1}) - 2\bar{\theta}_{-1}}{\bar{\theta}_o(X_1 + 1/X_1) - 2\bar{\theta}_1} \right)$$

Then, the value of $a_{II}$ is calculated from the temperature responses at the three positions within the given sample without reference to the presence or absence of the standard sample. To be specific, the equation (17) is easily obtained in this case by substituting $\bar{\theta}_o$, $\bar{\theta}_1$ and $\bar{\theta}_2$ in the equation (8) respectively for $x=0$, $x_1$ and $x_2$.

$$\bar{\theta}_o\left(\frac{X_1}{X_2} - \frac{X_2}{X_1}\right) + \bar{\theta}_1\left(X_2 - \frac{1}{X_2}\right) + \bar{\theta}_2\left(\frac{1}{X_1} - X_1\right) = 0 \quad (17)$$

In the equations (16) and (17), the values unknown are $\lambda_{II}$, $a_{II}$ and s. Owing to the nature of Laplace transform, s can assume an arbitrary finite, positive value so far as the equation (7) is capable of convergence. Practically, s is defined as described afterward. Thus, $\lambda_{II}$ and $a_{II}$ can be determined.

The thermal capacity $\rho_{II} c_{II}$ is fixed by the equation (18).

$$\rho_{II} c_{II} = \lambda_{II}/a_{II} \quad (18)$$

The basic principle of the method of this invention has been described with reference to an infinitely flat-shaped sample. This same method is also applicable to other samples of the one-dimentional system, i.e. semi-infinitely shaped samples, infinitely cylindrical solid or infinitely cylindrical hollow samples and spherical samples, providing that in contrast to the exponential function in the orthogonal coordinate system, the Bessel function is used in the cylindrical coordinate system and the Legendre function is used in the spherical coordinate system respectively.

In the case of a system illustrated in FIG. 2, for example, if the basic principle of the determination of thermal properties of a cylindrical solid or hollow sample is assumed to be equal to that of the plate-shaped sample described above, then the thermal diffusivity $a_{II}$ between the given sample (II) and the standard sample (I) is expressed by the equation (19).

$$\bar{\theta}_1 I_o(\sqrt{s/a_{II}}\, r_2) - \bar{\theta}_2 I_o(\sqrt{s/a_{II}}\, r_1) = 0 \quad (19)$$

The thermal conductivity $\lambda_{II}$ involved in this case is expressed by the equation (20).

$$\frac{\lambda_{II}}{\lambda_I} = \quad (20)$$

$$\sqrt{\frac{a_{II}}{a_I}} \frac{I_o(\sqrt{s/a_{II}}\, r_1)}{I_1(\sqrt{s/a_{II}}\, r_2)} \frac{1}{\bar{\theta}_1} \{A_I I_1(\sqrt{s/a_I}\, r_2) B_I K_1(\sqrt{s/a_I}\, r_2)\}$$

In these equations, $I_o$ stands for the zero-th modified Bessel function of the first type and $I_1$ and $K_1$ stand for the first modified Bessel functions respectively of the first and second types. $A_I$ and $B_I$ are integral constants to be fixed separately.

The principle of determination so far described necessitates incorporation of a thermometric element at at least one point within the sample. Now, the principle of determination which permits the determination of thermal properties without necessitating such incorporation of a thermometric element will be described with reference to a plate-shaped sample.

FIG. 3 is an explanatory diagram illustrating the principle of determination of thermal properties such as thermal conductivity, thermal diffusivity and thermal capacity by a procedure comprising the steps of placing two standard samples (I) and (III) in contact with the opposite surfaces of a given sample (II), measuring temperature responses one each in the boundary surfaces between the samples (I) and (II) and the samples (II) and (III) and within or on the surface of the standard samples (I) and (III), calculating Laplace integrals of the values found by the measurement, deriving a thermal conductivity equation from the Laplace integrals and subjecting the equation to Laplace transform to obtain relevant equations.

In the same manner as described above, $(\bar{q}_o)_I$ and $(\bar{q}_o)_{II}$ for the position $i=0$ indicated in the diagram are obtained. Since $(\bar{q}_o)_I$ equals $(\bar{q}_o)_{II}$, the following equation is obtained.

$$\lambda_{II} = (\bar{q}_o)_I \sqrt{\frac{a_{II}}{s}} \frac{X_L - X_L^{-1}}{\bar{\theta}_o(X_L + X_L^{-1}) - 2\bar{\theta}_L} \equiv f_1(a_{II}) \quad (21)$$

Similarly, $(\bar{q}_o)_{II}$ and $(\bar{q}_o)_{III}$ for the position $i=L$ are obtained. Here, since $(\bar{q}_o)_{II}$ equals $(\bar{q}_o)_{III}$, there is obtained the following equation.

$$\lambda_{II} = (\bar{q}_L)_{III} \sqrt{\frac{a_{II}}{s}} \frac{X_L - X_L^{-1}}{2\bar{\theta}_o - \bar{\theta}_L(X_L + X_L^{-1})} \equiv f_2(a_{II}) \quad (22)$$

It naturally follows that the formula (21) equals the formula (22). Thus, one obtains the following equation.

$$f_1(a_{II}) - f_2(a_{II}) = 0 \quad (23)$$

Accordingly, $a_{II}$ is found from the equation (23) and $\lambda_{II}$ from the equation (22) respectively. Besides, the thermal capacity $\rho_{II} c_{II}$ is found from the equation (24).

$$\rho_{II} c_{II} = (\lambda_{II}/a_{II}) \quad (24)$$

From the description given above of the principle, it is evident that thermal properties can be determined accurately under an arbitrary heating condition without reference to variation in the boundary condition so long as there are obtained Laplace integrals of those temperature responses to be secured at prescribed points of the samples involved. According to the principle illustrated in FIG. 3, basically accurate thermal properties can be determined under an arbitrary heating condition without necessitating incorporation of thermometric elements within the given sample (II).

It is, therefore, found necessary that the Laplace integration of the equation (10) should be performed to a point where the value of "t" is integrated to infinity ($\infty$). In this equation, however, the value of "$e^{-st}$" is a function which converges to 0 as the value of "t" increases. It is also necessary that the magnitude of $\theta_i(t)$, the temperature response necessary for the determination, should be confined within a limited range in which the thermal properties at that particular temperature will not be deprived of their significane.

As a natural consequence, the value of "$e^{-st}\theta_i(t)$" proves to be a function which converges to 0 as the value of "t" increases.

From the standpoint of the determination of thermal properties, therefore, there exists the time of determination, $t_{max}$, at which the equation (25) shown below is approximately satisfied.

$$\int_0^\infty e^{-st}\theta_i(t)dt = \int_0^{t_{max}} e^{-st}\theta_i(t)dt \tag{25}$$

Assume an ideal case wherein $t > o$ and a stepped temperature response of $\theta_i(t) = \theta_{oo}$ are both satisfied, and the following equation will hold good.

$$\int_0^{t_{max}} e^{-st}\theta_i(t)dt / \int_0^\infty e^{-st}\theta_i(t)dt = 1 - e^{-st_{max}} \tag{26}$$

This clearly shows that the extent of this approximation of the equation (25) depends on the magnitude of $s \cdot t_{max}$. The inventors, therefore, carried out a good many numerical tests with a view to finding the value of $s \cdot t_{max}$ and further verifying the method itself. To facilitate comprehension of the contents of the method of this invention, a typical numerical test will be described below.

Let us now assume a case in which stepped temperature responses $\theta_{-L}$, $o$ are produced with respect to $\theta_{-L}(t)$ under the condition that the temperature in the surface $x=1$ is constant or in other words, that $\theta(t)_l = 0$ is satisfied. By first fixing in advance the thermal properties of the standard sample (I) and the given sample (II) and $x_{-1}$, $x_1$, $x_2$, L and l and then proceeding to calculate $\theta_{-1}(t)$, $\theta_o(t)$, $\theta_1(t)$ and $\theta_2(t)$ through analytical solution, there are obtained the results as indicated by the solid lines in FIG. 4. The solid lines represent the numerical values of thermal properties determined by the method of the present invention on the assumption that they have been obtained through the test under discussion. In FIG. 4, $e^{-st}$ represented by $e^{-st}\theta_o(t)$ and $\theta_o$ representing the area indicated by the slanted lines are shown by way of example.

Figure 5:
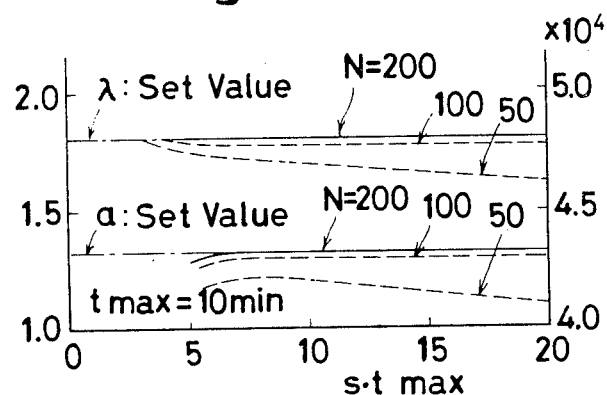
FIG. 5 is a diagram showing the relation between the numerical value of $s \cdot t_{max}$ and the number of samplings.

FIG. 5 shows the values of the thermal conductivity $\lambda_{II}$ and thermal diffusivity $a_{II}$ as functions of $s \cdot t_{max}$, which values are those obtained by calculating the various values of $\bar{\theta}$ through Simpton numerical integration (N as number of samplings) of the various values of $\theta(t)$ indicated in FIG. 4 and substituting the found values into the equations (16) and (17) respectively. From this graph it is evident that where the number of samplings, N, is 200 and the accuracy of numerical calculations is sufficiently high, the results are amply in agreement with the set values so far as $s \cdot t_{max}$ has a value exceeding a certain level (about 7 in this case). The difference of the results from the set values as observed when the value of $s \cdot t_{max}$ is in a lower range is ascribable to the fact that the approximation of the equation (25) is no longer satisfied. When the value of $s \cdot t_{max}$ is excessively increased, however, the value of $e^{-st}$ comes to converge to 0 while the value of t is still in its low range. This actually represents a case in which the data are evaluated with those temperature responses obtained within a short span of time. Thus, it is desirable to have a suitable upper limit fixed for the value of $s \cdot t_{max}$.

Practically the same results as those described above have been obtained through numerous other numerical tests and actual measurements without reference to the type of coordinate system, whether orthogonal or cylindrical. These results lead to the conclusion that when the value of $s \cdot t_{max}$ is limited within the range as defined by the equation (27), the approximation of the equation (25) is invariably satisfied so much as to offer great convenience to the determination.

$$8 \leq s \cdot t_{max} \leq 12 \tag{27}$$

Within the range of the equation (27), the value of s can be freely selected. The range of the value of $t_{max}$ can be freely selected insofar as the non steady behavior is so conspicuous as to involve enough change to permit comparison of temperature responses within that particular range. It is incidentally noted that within the range of the equation (27), the value of $\bar{\theta}$ can easily be obtained by graphical integration with relatively high accuracy. Further, temperature responses may be subjected to AD conversion and then automatically to Laplace integration or operation with the aid of a micro-computer.

When necessary, observance of the equation (28) is recommended for the determination of the value of $s \cdot t_{max}$.

$$s \cdot t_{max} = 8 \tag{28}$$

It is clear from the description given above that actually, the Laplace integration involved in the present invention need not be carried out for an infinite length of time; it is sufficient to carry it out only until the end of the time of determination, $t_{max}$. Thus, the determination can basically be carried out accurately by arbitrary heating, no matter how the boundary condition may be varied.

According to this invention, thermal properties such as thermal conductivity, thermal diffusivity and thermal capacity can be simultaneously determined.

Further, the thermal diffusivity $a_{II}$ can be fixed by the basic equation (17) in the case of a plate-shaped sample and by the basic equation (19) in the case of a cylindrical sample. Thus, it can be obtained from the temperature responses measured at the prescribed positions of the given sample even in the absence of the standard sample.

When one boundary condition of the given sample of any varying shape is established isothermally, by insulation or by the constancy of thermal input, the number of positions for the measurement of temperature response can be decreased. Accordingly, the method of the present invention can be practiced with ease. Besides, the numerical values of physical properties can be obtained from the equations which are derived by having a heat-flow meter installed in the surface of boundary in the place of the standard sample, measuring the lattice of heat flow, finding the Laplace integral of the lattice and equalizing the integer such as with the equation (15). Even in case where the initial temperature distribution is such as to be represented by a curve of second order, the determination can be accomplished with a simple compensation.

The method of the present invention can be practiced as effectively with a liquid or gaseous sample as with a solid sample insofar as the state or aggregate of the sample is proper.

The ordinary systems illustrated in FIGS. 1 and 2 can be converted into various, more convenient and more practical systems of measurement as by fixing thermometric points on the surface of the sample or suitably selecting the boundary condition. Examples of such modified systems will be touched upon below.

Table 1 gives examples of practical systems of measurement obtained by applying the basic principle of this invention to the plate-shaped sample, along with relevant equations.

Also concerning samples of the shape of solid cylinders and hollow cylinders, various applied systems of measurement are conceivable. With respect to the sample (I) illustrated in FIG. 2, for example, such applied systems are obtained as by keeping the outer periphery thereof at a constant temperature or in an insulated state, by using the central cylindrical portion thereof as the standard sample and the hollow cylindrical portion as the given sample, or by placing a cylindrical heating member at the center and placing on the periphery thereof both the given sample and the standard sample each of the shape of a hollow cylinder. A further modification may be accomplished as by placing a cylindrical heating member within an infinite sample. In all these modifications, the number of thermometric elements used are variable from one to another.

TABLE 1

Examples of practical systems of measurement

| Type | Position for measurement of temperature and symbol | | |
|---|---|---|---|
| Surface temperature on opposite faces | [I], [II] at $-L, 0, 1, 1$ | $a_{II}$ | $\bar{\theta}_o\left(\frac{X_l}{X_1} - \frac{X_1}{X_l}\right) + \bar{\theta}_1\left(X_l - \frac{1}{X_l}\right) + \bar{\theta}_l\left(\frac{1}{X_1} - X_1\right) = 0$ |
| | | $\lambda_{II}$ | $= \lambda_I \sqrt{\frac{a_{II}}{a_I}} \left(\frac{X_1 - \frac{1}{X_1}}{X_{-L} - \frac{1}{X_{-L}}}\right) \cdot \left\{\frac{\bar{\theta}_o\left(X_{-L} + \frac{1}{X_{-L}}\right) - 2\bar{\theta}_{-L}}{\bar{\theta}_o\left(X_1 + \frac{1}{X_1}\right) - 2\bar{\theta}_1}\right\}$ |
| Fixed temperature on one face and surface temperature on the other faces | [I], [II], $\theta_l = 0$ | $a_{II}$ | $\bar{\theta}_o\left(\frac{X_1}{X_l} - \frac{X_l}{X_1}\right) + \bar{\theta}_1\left(X_l - \frac{1}{X_l}\right) = 0$ |
| | | $\lambda_{II}$ | $= \lambda_I \sqrt{\frac{a_{II}}{a_I}} \left(\frac{X_1 - \frac{1}{X_1}}{X_{-L} - \frac{1}{X_{-L}}}\right) \cdot \left\{\frac{\bar{\theta}_o\left(X_{-L} + \frac{1}{X_{-L}}\right) - 2\bar{\theta}_{-L}}{\bar{\theta}_o\left(X_1 + \frac{1}{X_1}\right) - 2\bar{\theta}_1}\right\}$ |
| Insulation of heat on one face and surface temperature on opposite faces | [I], [II] at $-L, 0$ | $a_{II}$ | $2\bar{\theta}_o - \bar{\theta}_l\left(X_l - \frac{1}{X_l}\right) = 0$ |
| | | $\lambda_{II}$ | $= \lambda_I \sqrt{\frac{a_{II}}{a_I}} \left(\frac{X_l - \frac{1}{X_l}}{X_{-L} - \frac{1}{X_{-L}}}\right) \cdot \left\{\frac{\bar{\theta}_o\left(X_{-L} + \frac{1}{X_{-L}}\right) - 2\bar{\theta}_{-L}}{\bar{\theta}_o\left(X_l + \frac{1}{X_l}\right)}\right\}$ |
| Semi-infinite solid sample | [I], [II] at $-L, 0, 1$; $\theta \to 0$ in proportion to $x \to \infty$ | $a_{II}$ | $= \dfrac{sx_1^2}{\left\{l_n\left(\dfrac{\bar{\theta}_2}{\bar{\theta}_1}\right)\right\}^2}$ |
| | | $\lambda_{II}$ | $= \lambda_I \sqrt{\frac{a_{II}}{a_I}} \left(\frac{X_1 - \frac{1}{X_1}}{X_{-L} - \frac{1}{X_{-L}}}\right) \cdot \left\{\frac{2\bar{\theta}_{-L} - \bar{\theta}_o\left(X_{-L} + \frac{1}{X_{-L}}\right)}{\bar{\theta}_o\left(X_1 + \frac{1}{X_1}\right) - 2\bar{\theta}_1}\right\}$ |

Figure 6:
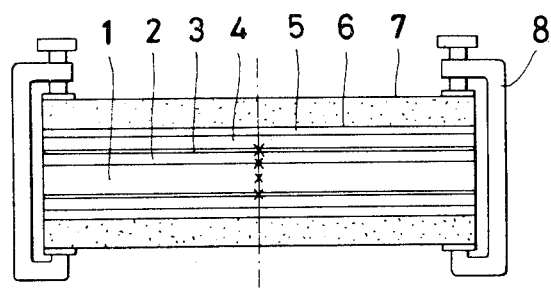
FIG. 6 is a schematic diagram illustrating a typical test unit formed for testing a plate-shaped sample.

Now, a preferred embodiment of this invention involving use of a plate-shaped sample will be described with reference to the accompanying drawing. FIG. 6 is a schematic diagram of a test unit wherein the determination is performed in the manner shown in the first column of Table 1.

As a given sample 1, there is used a pair of intimately adjoining circular plates of acrylic resin and soda glass, each about 5 mm in thickness and 150 mm in diameter. A Pyrex glass circular plate 3 mm in thickness is used as a standard sample 2. As thermometric elements 3, 0.1-$\phi$ Alumel-Chromel thermocouples are used, with the contact points thereof fixed at the centers of the circular samples.

Teflon sheets 4, 1 mm in thickness, are placed on the opposite outer faces of the samples for the purpose of causing the samples to be adjoined uniformly to each other, copper plates 5, 3 mm in thickness, are disposed on the opposite outer surfaces of the Teflon sheets 4 for the purpose of uniformizing the field of temperature in the radial direction, brass plates 6, 3 mm in thickness, circularly convexed slightly in the direction of the samples so as to acquire resiliency are disposed on the opposite outer surfaces of the copper plates, and acrylic resin plates 7, 10 mm in thickness, are placed on the opposite outer surfaces of the brass plates for the purpose of retarding the temperature responses of the samples to the extent required. All these component plates are united into one complete test unit by uniformly clamping the outer sides of the acrylic resin plates 7, 7 with clamp means 8.

Figure 7:
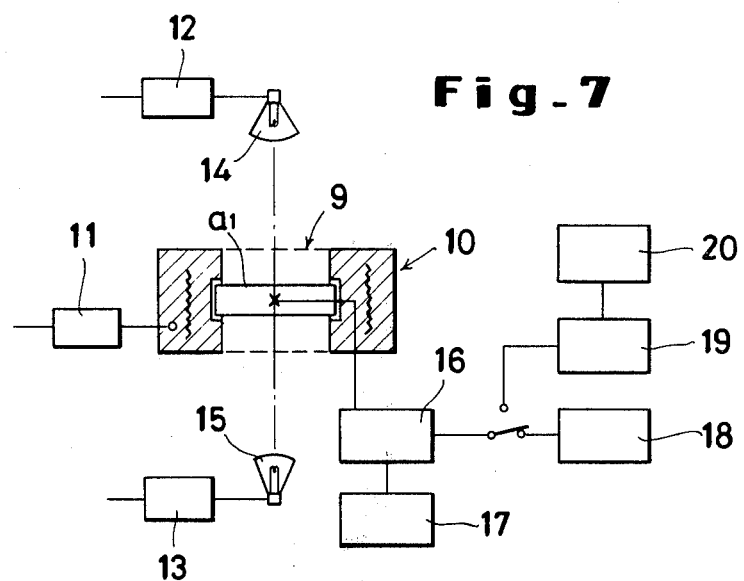
FIG. 7 is a schematic diagram illustrating a test apparatus using the test unit of FIG. 6.

FIG. 7 is a system diagram of the apparatus used for determination by the method of the present invention. The test unit $a_1$ formed as described above is set in position at the center of a constant temperature bath 10 provided with glass windows 9 one each in the upper and lower sides thereof. The temperature inside this constant temperature box 10 is maintained at a prescribed level by means of a Slidac 11. After the numerical values indicated on the thermometric elements within the test unit $a_1$ are found to be equal, Slidacs 12, 13 are put into operation to supply energy from the infrared lamps 14, 15 to the test unit $a_1$. The thermal electromotive force from the thermocouples of the thermometric elements is recorded by a balancing recorder 18 through the medium of a changeover switch 16 and a voltage compensator 17. When desired, the numerical value indicated by the digital voltmeter 19 can be recorded by a printer 20.

FIG. 8 illustrates one typical record of temperature responses obtained by the test. Numerals 1, 2, 3 and 4 in the diagram correspond to the changes of temperature responses at the positions of thermometric elements (marked by X's in FIG. 6) in descending order. The recorded values are read out at time intervals, with the Laplace integration carried out by the Simpson Method.

Figure 9:
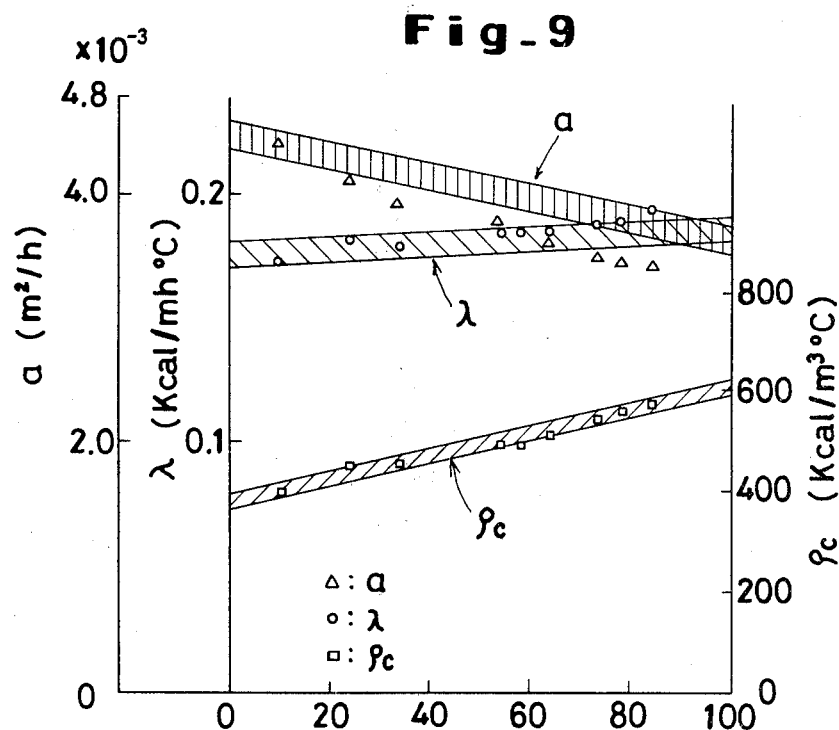
FIG. 9 is a diagram showing thermal properties of an acrylic resin plate.

FIG. 9 shows the results obtained by a determination carried out with respect to acrylic resin plates. In the diagram, the dots represent the results actually obtained by the determination according to the method of this invention and the strips indicated by slanted lines represent the ranges of empirical values proposed by Okada et al(J. of JSME, 79 (1976) 247).

FIG. 10 shows the results of a determination with respect to soda glass plates. In the diagram, the solid line and the dotted lines represent the empirical values proposed by Katayama et al (Trans. JSME, 34 (1968) 2012).

These results of the method of the present invention are in satisfactory agreement with the results of the other experiments and enjoy high reproducibility.

Now, a preferred embodiment of this invention involving a cylindrical solid or hollow sample will be described. FIG. 11 is a schematic diagram of a cylindrical sample. The test unit $a_2$ is formed by placing a circular hollow standard sample 2 on the outer periphery of a cylindrical sample 1 subjected to the determination, disposing a brass tube 21 on the outer periphery of the standard sample 2, winding a heater 23 helically up the outer periphery of the brass tube 21 so as to apply heat during the test, further having a heater 22 wound helically up the outer surface of the wound heater 23 and filling the annular space formed between the brass tube 21 and the standard sample 2 with alumina powder 24 for the purpose of enhancing the thermal conductivity.

The thermometric elements 3 (indicated by X's) are located in the axis of the given sample 1, in the interface between the given sample 1 and the standard sample 2 and on the outer peripheral surface of the standard sample 2.

FIG. 12 is a schematic diagram of the test apparatus constructed as described above. The test unit $a_2$ is stowed inside a constant temperature bath 10 and the heater 22 for the application of heat during the test and the heater 23 are connected to a Slidac 28. The thermal electromotive force from the thermometric elements 3 is recorded by the balancing recorder 18 through the medium of a changeover switch 16 and a voltage compensator 17.

Figure 13:
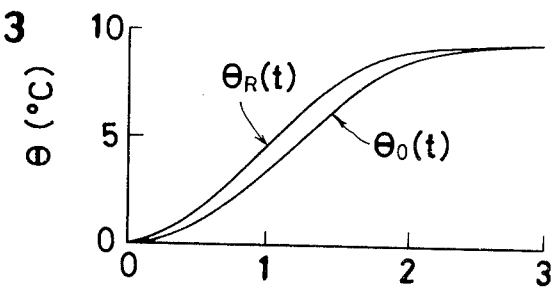
FIG. 13 is a diagram showing a typical record of temperature responses obtained of 18-8 stainless steel.
Figure 14:
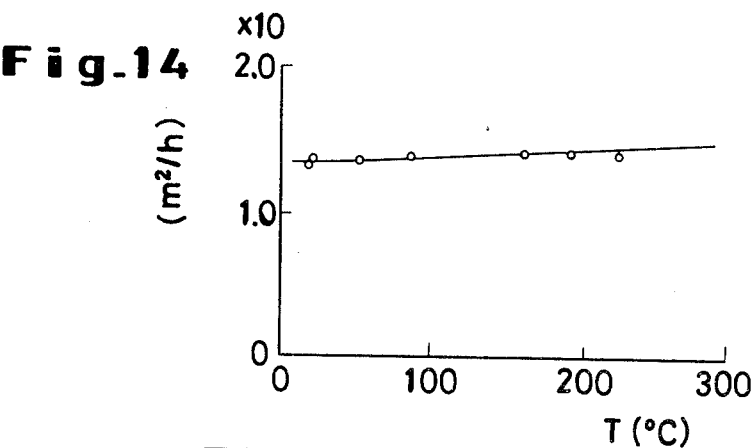
FIG. 14 is a diagram showing the results of the determination of thermal diffusivity of the same stainless steel.

FIG. 13 illustrates one typical record of temperature responses obtained in the determination of thermal conductivity of an 18-8 stainless steel by use of the test apparatus described above. FIG. 14 shows the results of the determination. The results indicated by the dots in the diagram are quite satisfactorily in agreement with the values of prior literature (Touloukian, TPRC Data Sek.) represented by the solid line with an accuracy of within about 1%.

Figure 15:
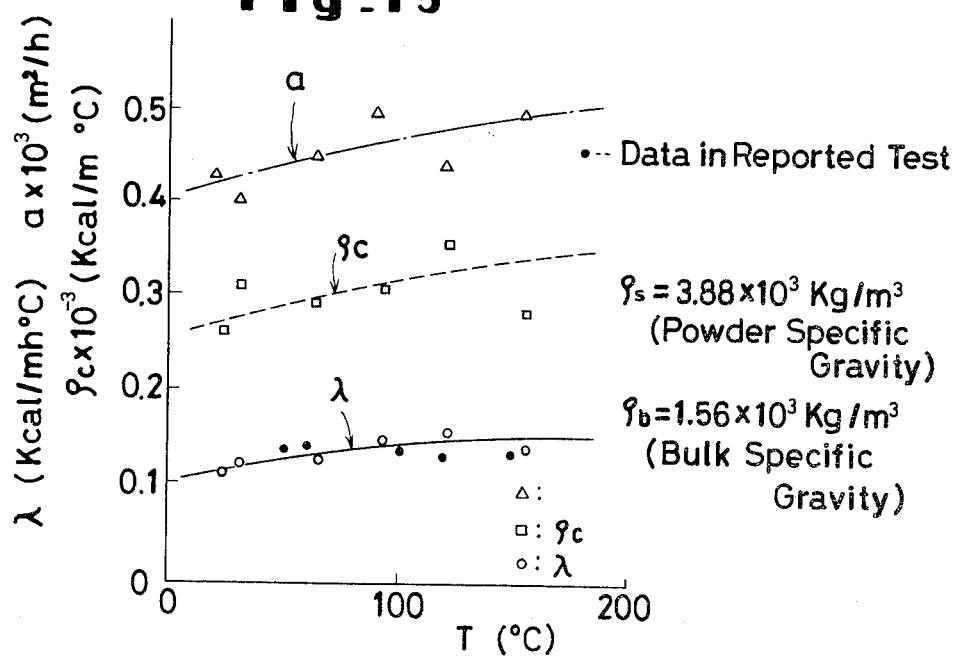
FIG. 15 is a diagram showing the results of simultaneous determination performed on alumina powder as a sample.

To illustrate a typical application of the method of this invention to the simultaneous determination of thermal conductivity, thermal diffusivity and thermal capacity, the physical properties of alumina powder were determined. The results are shown in FIG. 15. Since the numerical values reported in the TPRC Data Book mentioned above are limited to those of thermal conductivity, the results of FIG. 15 can be compared only with such data on thermal conductivity. This comparison also reveals fairly good agreement.

Figure 16:
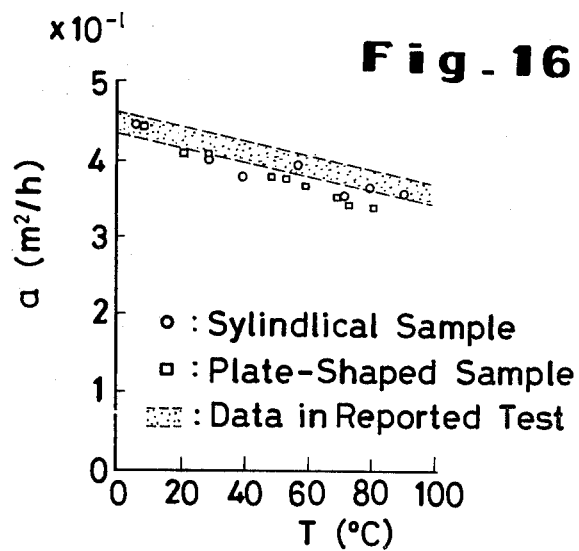
FIG. 16 is a diagram showing the thermal diffusibility of an acrylic resin sheet in comparison with the results of a test by other researchers.

FIG. 16 compares the data on thermal conductivity obtained of the acrylic resin sample with those obtained of a plate-shaped acrylic resin sample and those obtained by Okada et al in their test reported (J. of JSME, 79, (1967) 247). A review of the diagram shows good agreement of the results under comparison.

Figure 17:
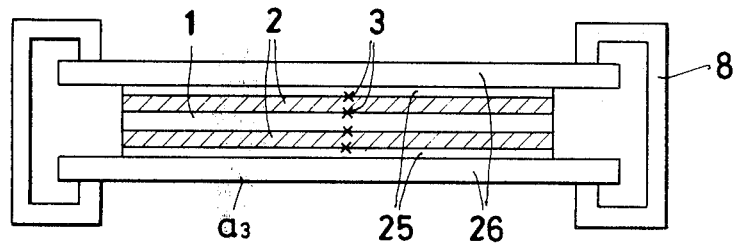
FIG. 17 is a schematic diagram illustrating a typical test unit used for the determination of thermal properties on the basis of the principle illustrated in FIG. 3.

FIG. 17 illustrates a typical construction of the test unit used for the determination of thermal properties on the basis of the principle depicted in FIG. 3.

This test unit is formed by placing standard samples 2, 2 on the outer surfaces of a given sample 1 with unknown thermal properties after the outer surfaces have been coated with silicone oil for the purpose of decreasing the contact thermal resistance to a negligibly small level, disposing tight-adhesion cushions 25, 25 (resilient plates such as of Neoprene 1.5 mm in thickness in the present preferred embodiment) on the outer surfaces of the standard samples 2, 2 similarly after the outer surfaces have been coated with silicone oil, disposing heat-uniformizing plates 26, 26 (brass plates 8 mm in thickness in the present preferred embodiment) on the outer surfaces of the cushions 25, 25 for the purpose of uniformizing the field of temperature in the radial direction, and having thermometric element 3 inserted centrally one each in the surfaces of boundary between the given sample 1 and the standard samples 2, 2 and in the surfaces of boundary between the standard samples 2, 2 and the cushions 25, 25. For practical purpose, the thermocouples (thermometric elements) are disposed on the opposed surfaces of the standard samples so that the given sample can be disposed simply by insertion into the intervening space formed therebetween.

The laminated combination of given sample 1, standard samples 2, 2, cushions 25, 25 and heat-uniformizing plates 26, 26 formed as described above is tightly joined with uniform pressure by means of a clamp means 8 such as vices to give rise to the test unit $a_3$. Since the cushions 25, 25 and the heat-uniformizing plates 26, 26 are additionally capable of alleviating the temperature responses of the samples, they can be designed so as to permit free adjustment of their thickness.

Figure 18:
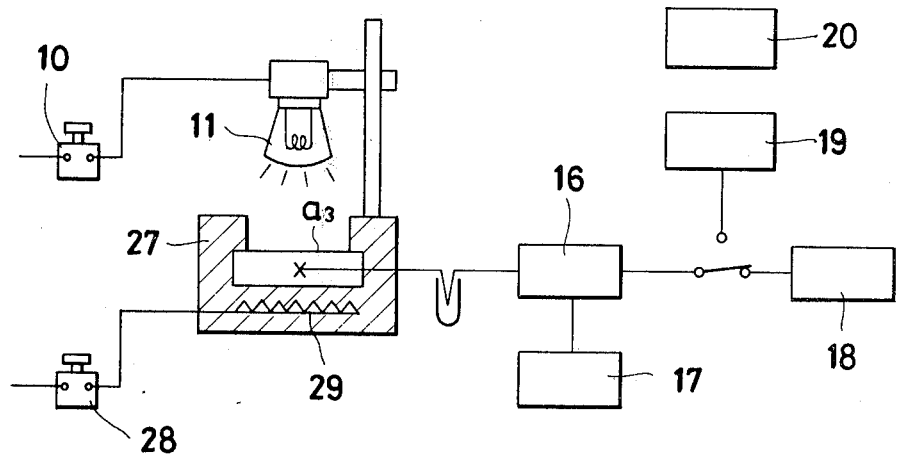
FIG. 18 is a schematic diagram illustrating a typical test apparatus using the test unit of FIG. 17.

FIG. 18 illustrates one typical example of the apparatus for the determination according to the principle shown in FIG. 3. In this apparatus, the test unit $a_3$ is stowed in a copper block 27 with an open top. Into this copper block 27, a heater 29 adapted to permit free adjustment of the feed rate of heat by means of a Slidac 23 is inerted. Above the test unit $a_3$ is disposed an infrared lamp 31 which is adapted to permit free adjustment of the feed rate of heat by means of a Slidac 30.

The thermometric system of the thermometric elements 3, 3 is composed of a changeover switch 16, a voltage compensator 17, a balancing recorder 18, a digital voltmeter 19 and a printer 20.

The determination by use of this test apparatus is initiated by first confirming that the numerical values indicated by the thermometric elements 3, 3 are equal, then adjusting the Slidac 30 to supply a fixed amount of energy from the infrared lamp 31 to the test unit $a_3$ and further adjusting the Slidac 28 so as to have the heater 29 supply to the test unit $a_3$ a heat adjusted to increase and decrease along the course of time. In this determination, the temperature responses in the aforementioned surfaces of boundary are measured by the thermometric elements 3, 3 and recorded. These temperature responses are recorded by causing the thermal electromotive force from the thermometric elements 3, 3 to be applied to the balancing recorder 18 through the medium of a changeover switch 16 and a voltage compensator 17. The recorded numerical values are read out at time intervals and the Laplace integration of the values is carried out by the Simpson Method.

When desired, the recorded numerical values may be obtained by causing the numerical values indicated on the digital voltmeter 19 to be recorded on the printer 20. Otherwise, the numerical values of the digital voltmeter 19 may be subjected to AD conversion and then processed by the microcomputer.

The preferred embodiment described above involves a construction wherein the heat adjusted to increase and decrease along the course of time is supplied from the heater to the lower surface of the test unit $a_3$. This construction of the test apparatus can be modified in various ways as, for example, by using a constant temperature water bath in the place of the heater 29, so that the lower surface of the test unit $a_3$ will be maintained at a fixed temperature by means of the water of the bath during the determination.

Table 2 shows the results of the test performed in accordance with the aforementioned method by using in the test unit $a_3$ differing materials as indicated in the same table.

TABLE 2

| | Material of sample used for test | |
|---|---|---|
| | A | B |
| (1) Given sample | Teflon (5 mm) | Soda glass (5 mm) |
| (2) Standard sample | Soda glass (5 mm) | Soda glass (5 mm) |
| (3) Tight-adhesion cushion | Neoprene rubber (1.5 mm) | Neoprene rubber (1.5 mm) |
| (3) Heat-uniformizing plate | Brass plate (8 mm) | Brass plate (8 mm) |

The combinations (A) and (B) are used so that the lower surfaces of the test units are heated by the heater 29, with the changes of temperature at the prescribed locations recorded. In the test, the greatest change of temperature is limited to within 10° C.

FIG. 19 shows the results of the test using the combination (A). The data of thermal conductivity thus obtained are compared with the data proposed by Fritz et al (Chem. Ing. Techn. 37 (1951) 1118).

FIG. 20 shows the results of the test using the combination (B). According to the diagram, the data of thermal diffusivity are seen to be accurate to within about 9% and those of thermal conductivity to be accurate to within less than 1%. The straight lines indicated by dotted lines represent the results of the test by Katayama et al (Trans. JSME 34 (1968) 2012) which have heretofore been accepted as being of highest possible accuracy. From the diagram, it is noted that the results of the present test are quite satisfactorily in agreement with Katayama et al's results.

As is evident from the description given above, this invention enables thermal properties to be determined simply through measurement of temperature responses at various prescribed positions under arbitrary temperature increasing and heating condition. Because of the arbitrariness of such conditions, the test apparatus required for practicing the method of this invention is simple as compared with that required by the conventional method and the operation of the apparatus calls for no skill on the part of the operator. Further, the results of this test are evaluated on the basis of all the data obtained within the time of measurement. Thus, the method of this invention produces numerical values of high accuracy. Owing to these advantages, the method of the present invention overcomes all the problems involved by the conventional method. The present invention, accordingly, provides an epochal method capable of greatly facilitating the determination of thermal properties.

Particularly in the preferred embodiment illustrated in FIG. 3, the thermal properties of a given plate-shaped sample can be determined under an arbitrary boundary condition and an arbitrary heating condition simply by causing the sample to be interposed in an intimately adjoining manner between two plate-shaped standard samples without entailing technical problems such as fabrication of samples and incorporation of extra thermometric elements. The determination by this method produces results of high accuracy.

What is claimed is:
1. A method for the simultaneous determination of thermal properties by arbitrary heating, which method comprises:
   placing a given sample in intimate contact with a standard sample;
   applying a flow of heat to the two samples in a direction perpendicular to a surface of contact between the two samples by use of a heat source disposed outside the two samples;

measuring temperature responses in the surface of contact of said two samples, said measurements further being made at least at one point within the standard sample and at most at two points within the given sample;

transmitting the measured temperature responses through an A/D convertor to a Laplace integrator to obtain Laplace integrals of the temperature responses; and transmitting the Laplace integrals to an operator;

whereby the thermal properties such as thermal conductivity, thermal diffusivity and thermal capacity are determined simultaneously.

2. The method set forth in claim 1, wherein:
the flow of heat is applied to a surface of the standard sample, said surface being opposite to the surface of contact of said two samples.

3. The method set forth in claim 1, wherein:
the flow of heat is applied to a surface of the given sample, said surface being opposite to the surface of contact of said two samples.

4. The method set forth in claim 1, wherein the flow of heat is applied to surfaces of the standard sample and the given sample, said surfaces being opposite to the surface of contact of said two samples.

5. The method set forth in claim 1, wherein the standard sample and the given sample are both in the shape of one of flat plates, cylinders, hollow cylinders, spheres, and hollow spheres.

6. A method for the simultaneous determination of thermal properties by arbitrary heating, which method comprises:

placing a given sample in intimate contact with a standard sample;

applying a flow of heat to the two samples in a direction perpendicular to a surface of contact between the two samples by use of a heat source disposed outside the two samples;

measuring temperature responses in the surface of contact of said two samples, said measurements further being made at one point within one of the standard sample and a surface of the standard sample, said surface of the standard sample being opposite the surface of contact of said two samples, said measurements being further made at most at two points within one of the given sample and a surface of the given sample, said surface of the given sample being opposite to the surface of contact of said two samples;

transmitting the measured temperature responses through an A/D convertor to a Laplace integrator to obtain Laplace integrals of the temperature responses; and transmitting the Laplace integrals to an operator;

whereby the thermal properties such as thermal conductivity, thermal diffusivity, and thermal capacity are determined simultaneously.

7. The method set forth in claim 6 wherein:
the flow of heat is applied to a surface of the standard sample, said surface of the standard sample being opposite to the surface of contact of said two samples.

8. The method set forth in claim 6, wherein:
the flow of heat is applied to a surface of the given sample, said surface of the given sample being opposite to the surface of contact of said two samples.

9. The method set forth in claim 8, wherein:
the flow of heat is applied to surfaces of the standard sample and the given sample, said surfaces being opposite to the surface of contact of said two samples.

10. The method set forth in claim 6, wherein:
the standard sample and the given sample are both in the shape of one of flat plates, cylinders, hollow cylinders, spheres, and hollow spheres.

11. A method for the simultaneous determination of thermal properties by arbitrary heating, which method comprises:

placing a given sample having two exterior surfaces between two standard samples so that both exterior surfaces of the given sample come into intimate contact with the respectively inner surfaces of the standard samples;

applying a flow of heat to the three samples in a direction perpendicular to the surfaces of contact between the given sample and the standard samples by use of a heat source disposed outside the three samples;

measuring temperature responses at two points in the surfaces of contact of the three samples, one of said two points being located in each of said surfaces of contact, said measurements being further made at two additional points, each one of said two additional points being located within one of said two standard samples and surfaces of said two standard samples opposite to said surfaces of contact of said two standard samples and said given sample;

transmitting the measured temperature responses through an A/D convertor to a Laplace integrator to obtain Laplace integrals of the temperature responses; and transmitting the Laplace integrals to an operator;

whereby the thermal properties such as thermal conductivity, thermal diffusivity, and thermal capacity are determined simultaneously.

12. The method set forth in claim 11, wherein:
the flow of heat is applied to a surface of one of the standard samples, said surface of said one standard sample being opposite to said surface of contact between said one standard sample and said given sample.

13. The method set forth in claim 11, wherein:
the flow of heat is applied to the surfaces of the standard samples, said surfaces of said standard samples being opposite to said surfaces of contact between said two standard samples and said given sample.

14. The method set forth in claim 11, wherein:
the standard samples and the given sample are each in the shape of one of flat plates, cylinders, hollow cylinders, spheres, and hollow spheres.

* * * * *